(12) United States Patent
Boekelman

(10) Patent No.: US 7,564,032 B2
(45) Date of Patent: Jul. 21, 2009

(54) GAS SENSOR

(75) Inventor: Willem Antonius Boekelman, Venlo (NL)

(73) Assignee: Berli B.V., Venlo (NL)

( * ) Notice: Subject to any disclaimer, the term of this patent is extended or adjusted under 35 U.S.C. 154(b) by 454 days.

(21) Appl. No.: 10/573,088

(22) PCT Filed: Sep. 20, 2004

(86) PCT No.: PCT/NL2004/000652

§ 371 (c)(1),
(2), (4) Date: Mar. 23, 2006

(87) PCT Pub. No.: WO2005/029048

PCT Pub. Date: Mar. 31, 2005

(65) Prior Publication Data

US 2006/0290934 A1 Dec. 28, 2006

(30) Foreign Application Priority Data

Sep. 24, 2003 (NL) .................................. 1024364

(51) Int. Cl.
*G01N 21/00* (2006.01)
(52) U.S. Cl. ................................................. 250/338.1
(58) Field of Classification Search ............... 250/338.1
See application file for complete search history.

(56) References Cited

U.S. PATENT DOCUMENTS

| 3,120,608 | A |   | 2/1964  | Bird              |
|-----------|---|---|---------|-------------------|
| 4,382,656 | A |   | 5/1983  | Gilby             |
| 4,899,053 | A |   | 2/1990  | Lai et al.        |
| 5,125,742 | A |   | 6/1992  | Wilks, Jr.        |
| 5,734,165 | A |   | 3/1998  | Unal et al.       |
| 5,977,546 | A |   | 11/1999 | Carlson           |
| 6,097,034 | A | * | 8/2000  | Weckstrom et al. ...... 250/495.1 |

FOREIGN PATENT DOCUMENTS

| DE | 101 24 055 A | 11/2002 |
| EP | 0457624 A1   | 11/1991 |
| GB | 1 538 833 A  | 1/1979  |

\* cited by examiner

*Primary Examiner*—David P Porta
*Assistant Examiner*—Marcus H Taningco
(74) *Attorney, Agent, or Firm*—Hoffmann & Baron, LLP; John S. Sopko

(57) ABSTRACT

A gas sensor includes at least two light source, projection optics and a light-reflecting chamber provided with at least one light entry opening. The gas sensor further includes a detector that cooperates with the chamber, by means of which detector light from the light source can be detected. The at least two light sources can each be projected on a light entry opening of the chamber by means of the projection optics.

21 Claims, 4 Drawing Sheets

GAS SENSOR

CROSS-REFERENCE TO RELATED APPLICATIONS

This application is the National Stage of International Application No. PCT/NL2004/000652, filed Sep. 20, 2004, which claims the benefit of Netherlands Application No. NL 1024364, filed Sep. 24, 2003, the contents of which is incorporated by reference herein.

FIELD OF THE INVENTION

The invention relates to a gas sensor comprising at least one light source, projection optics and a light-reflecting chamber provided with at least one light entry opening, which gas sensor further comprises a detector that cooperates with the light-reflecting chamber, by means of which detector light from the light source can be detected.

DISCUSSION OF THE PRIOR ART

With such a gas sensor, which is known from U.S. Pat. No. 5,734,165, a light source is projected on the light entry opening of a light-reflecting chamber via a mirror. The light from the light source is deflected by a mirror grating in the light chamber and directed to the detector. The light is analysed by means of the detector, and from the analysed light at least the gas concentration of a gas is determined.

Gases can be selectively detected by making use of an infrared spectrometer, for example, and of their specific absorption characteristics in the infrared spectral range.

Absorption of the light takes place in the gas that is present in the light path between the light source and the detector. The length of said light path depends on the gas that is to be detected.

The stability and accuracy of the gas sensor are influenced inter alia by the mechanical strength, thermal drift, changes in the humidity level, fouling of the components in the light path between the light source and the detector, ageing of the light source and the detector, etc. These effects influence the light to be detected by means of the detector and can thus lead to a deviation in the determination of the gas concentration of the gas to be measured.

In particular variations in the position of the light source with respect to the detector, for example due to thermal effects, will lead to an uncontrolled change in the light to be detected by means of the detector when using the gas sensor according to the aforesaid U.S. Pat. No. 5,734,165, which will lead to undesirable deviations in the gas concentration to be determined therefrom.

SUMMARY OF THE INVENTION

The object of the invention is to provide a gas sensor which is relatively insensitive to influences such as thermal drift, fouling, ageing and mechanical changes.

The relative insensitivity to thermal drift, fouling and ageing of the gas sensor according to the invention is achieved in that the gas sensor comprises at least two light sources, which can each be projected on a light entry opening of the chamber by means of the projection optics.

In this way it is possible to use one light source as a reference light source, whilst at least one other light source is suitable for gas detection, for example in cooperation with an associated wavelength-determining element.

The relative insensitivity to mechanical changes is achieved in that the light from a light source, which is projected on the light entry opening of the chamber by means of the optics, is reflected in the chamber a number of times on average, as a result of which the light distribution is homogenised, as it were.

The use of projection optics makes it possible to use a relatively large light source, which can be projected on a reduced scale on a relatively small light entry opening. In this way, too, the sensitivity to mechanical changes is reduced.

The use of two light sources and a single detector makes it possible to obtain a gas sensor that does not comprise any moving parts, which renders the gas sensor less sensitive to failure.

It has furthermore become apparent that light sources remain relatively stable with the passage of time, which contributes to the long-term accuracy of the gas sensor.

In an embodiment of the gas sensor according to the invention, the gas sensor is provided with at least two light sources, which can each be projected on the same light entry opening of the chamber by means of projection optics.

Since both light sources can be projected on one and the same light entry opening, the gas sensor will be even less sensitive to small changes in the gas sensor mechanics, and the light paths between the light sources and the detector are substantially identical.

In an embodiment of the gas sensor according to the invention, a wavelength-determining element is disposed between at least one light source and the detector.

This makes it possible to use light beams having different wavelengths, which function as a reference light beam and a light beam for measuring the desired gas respectively.

In an embodiment of the gas sensor according to the invention, the projection optics comprises at least one projection mirror.

The occurrence of light absorption phenomena associated with the use of a lens is prevented by using a mirror.

In an embodiment of the gas sensor according to the invention, the mirror comprises a number of segments, a first group of which segments cooperates with the first light source whilst the second group of segments cooperates with the second light source.

In this way, the light paths of the light beams from the light source will be substantially identical. In addition, the effect of ageing and fouling of the mirror will be the same for both light sources when such a segmented mirror is used, and it is possible to obtain a symmetrical incidence of light in the light-reflecting chamber. This makes the gas sensor relatively insensitive to changes in the gas sensor mechanics.

The segments of the first group preferably have a first focal point, whilst the segments of the second group have a second focal point.

In an embodiment, the segments of the two groups are evenly distributed over the mirror.

In an embodiment of the gas sensor according to the invention, the light sources are disposed on the same side of the detector.

In this way it is possible to position the light sources relatively close together, so that the light beams from the light sources will follow substantially the same light paths to the chamber. This reduces the sensitivity to changes in the mechanics even further.

In an embodiment, the light sources are spaced apart by a centre distance in the order of the diameter of the light sources. This, too, achieves that the light beams from the light sources substantially coincide.

In an embodiment of the gas sensor according to the invention, the light-reflecting chamber is of square cross-section, at least one side of which cross-section has a dimension in the order of the dimension of a light-receiving element of the detector or of the dimension of the projection of the light source.

As a result of this shape of the light-reflecting chamber, an optimum homogenising effect is obtained. In an embodiment, the chamber is tapered, as a result of which the light is concentrated in the direction of the detector.

In this way, the light that is present in the chamber is reflected at different angles on different positions of the chamber, as a result of which the light intensity measured by the detector remains the same, substantially independently of the position of the light source that is projected on the light entry opening.

Because the light exit opening of the chamber is disposed close to the detector surface, the relative position is guaranteed, as a result of which any mechanical changes will not affect this part of the sensor and drift of the measurements caused by the light shifting over the detector surface is thus prevented.

The claims and advantages will be more readily appreciated as the same becomes better understood by reference to the following detailed description and considered in connection with the accompanying drawings in which like reference symbols designate like parts.

DETAILED DESCRIPTION OF PREFERRED EMBODIMENTS

Figure 1:
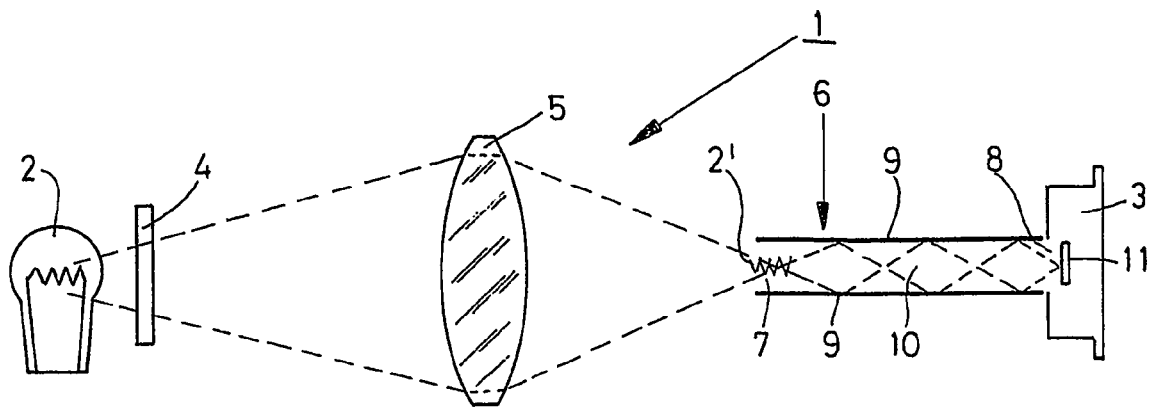
FIG. 1 is a schematic view of the basic principle of a gas sensor according to the invention.

FIG. 1 shows the basic principle of a gas sensor 1 according to the invention, which comprises a light source 2 and a detector 3. A light path extends between the light source 2 and the detector 3, in which light path a wavelength-determining element in the form of an infrared filter 4, projection optics in the form of a lens 5 and a light-reflecting, channel-shaped chamber 6 are disposed. The light-reflecting chamber 6 is elongate in shape and has a light entry opening 7 on a side facing towards the lens 5 and a light exit opening 8 on a side facing towards the detector 3. The light source 2 is projected on the light entry opening 7 as the light source 2' by means of the lens 5. The chamber 6 comprises a number of light-reflecting walls 9, which bound a cavity 10 in which the light from the light source 2 is reflected a number of times before the light exits the chamber 6 via the light exit opening 8 and falls on a light-sensitive surface 11 of the detector 3. The light source 2 emits light which is filtered by the filter 4, so that only infrared light having a specific, desired wavelength will be passed on in the direction of the detector 3, said wavelength being dependent on the gas that is to be detected. Depending on the concentration of the gas to be detected, which is present in the space in which the gas sensor 1 is present, a certain part of the infrared light will be absorbed.

On the basis of the amount of infrared light measured by the detector 3, the concentration of a $CO_2$ gas, for example, in the gas that is present in the space is determined. This is important, for example in order to determine the quality of the gas in a space in which persons are present, such as a living-room, an office, etc. Said gas is the air that is present in the living-room. Since the light path in the chamber 6 is relatively long, the light in the chamber 6 is homogenised relatively well, as a result of which the light path is relatively insensitive to mechanical changes.

The chamber 6 is preferably channel-shaped, the length preferably being at least three times greater than the cross-sectional dimension so as to ensure that the light in the chamber 6 is properly mixed. Preferably, said cross-sectional dimension is of the same order as the dimension of the light-sensitive surface 11 of the detector 3. Commercially available detectors 3 have a light-sensitive surface 11 of a few square millimetres. The walls 9 of the chamber 6 are preferably made of a metal that reflects light well, for example gold, so that an optimum reflection is obtained. The cross-section of the chamber 6 is preferably square-shaped, for example oblong or square. Preferably, the chamber is tapered in the longitudinal direction of the chamber 6, the cross-sectional area near the entry opening 7 and the cross-sectional area near the exit opening preferably differing from each other by a factor of up to 5.

Figure 2:
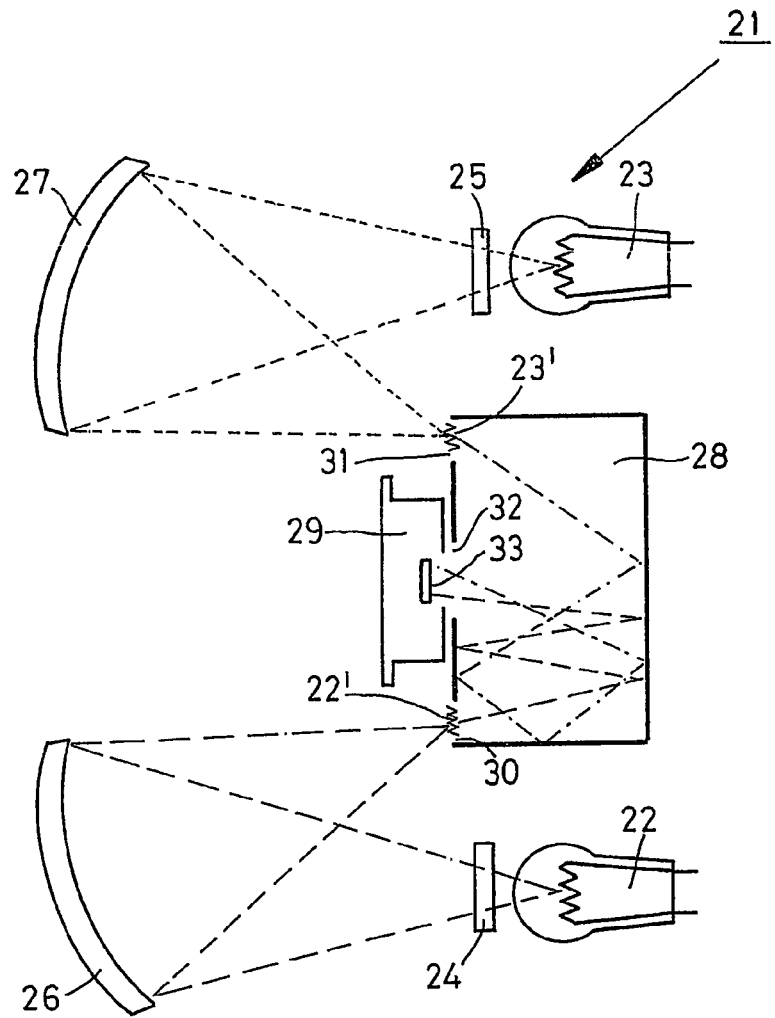
FIG. 2 is a schematic view of a first embodiment of a gas sensor according to the invention.

FIG. 2 shows a first embodiment of a gas sensor 21 according to the invention, which comprises two light sources 22, 23, filters 24, 25 disposed in front of the light sources 22, 23, projection optics in the form of curved mirrors 26, 27 disposed in front of said filters 24, 25, a chamber 28 and a detector 29. The chamber 28 is provided with two light entry openings 30, 31, on which the light sources 22, 23 are projected as light sources 22', 23' by means of the mirrors 26, 27. The chamber 28 furthermore comprises a light exit opening 32 centrally disposed between the light entry openings 30, 31, opposite a light-receiving surface 33 of the detector 29.

The filters 24, 25 each transmit infrared light of a different wavelength. If the presence of $CO_2$ is detected by means of the sensor, the wavelength for the filter 24 will be 4.3 µm, for example, and the wavelength for the reference filter 25 will be 4 µm, for example.

By means of the light source 22 and the associated filter 24, light having a wavelength at which $CO_2$ absorbs maximally is transmitted, which light is directed towards the light entry opening 30 via the mirror 26, after which the light is reflected in the cavity bounded by the chamber 28 a number of times before the light reaches the light-sensitive surface 33 of the detector 29. By means of the detector 29, the concentration of $CO_2$ gas that is present in a gas (air) surrounding the gas sensor 21 is determined. Light at which $CO_2$ absorbs minimally is transmitted by means of the filter 25, which light is subsequently analysed in the same manner by means of the detector 29. The light source 23 functions as a reference. If a change occurs in the light being emitted by the light source 23 and being detected by the detector 29, this is an indication that a change has occurred in the gas sensor 21, such as a decrease of the sensitivity of the detector, fouling of one or more components of the sensor, etc. Subsequently, the measured change can be taken into account in the determination of the $CO_2$ concentration by means of the light source 22. Preferably, the light sources 22, 23 are alternately turned on and off at short intervals, so that only the light from a single light source 23 or 24 needs to be analysed by means of the detector 29. It is also possible, however, to use a detector by means of which the light from both light sources 22, 23 can be simultaneously measured and analysed.

Figure 3:
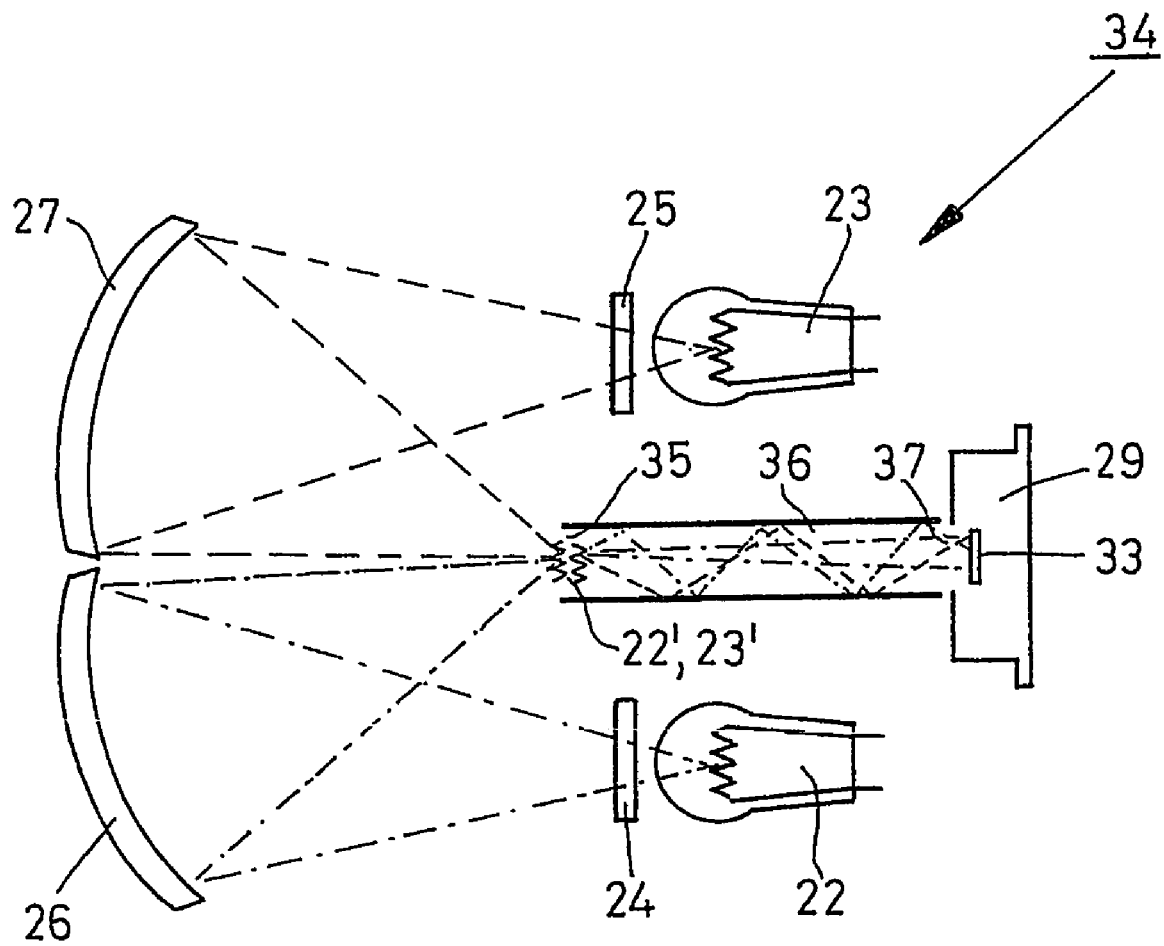
FIG. 3 is a schematic view of a second embodiment of a gas sensor according to the invention.

FIG. 3 shows a second embodiment of a gas sensor 34 according to the invention, which is different from the gas sensor 21 that is shown in FIG. 2 in that the two light sources 22, 23 are projected on the same light entry opening 35 of a chamber 36. The chamber 36 is provided with a light exit opening 37 on a side remote from the light entry opening 35, opposite which a light-sensitive surface 33 of a detector 29 is disposed. Compared to the gas sensor 21, the gas sensor 34 has the advantage that practical identical light paths are formed.

Figure 4:
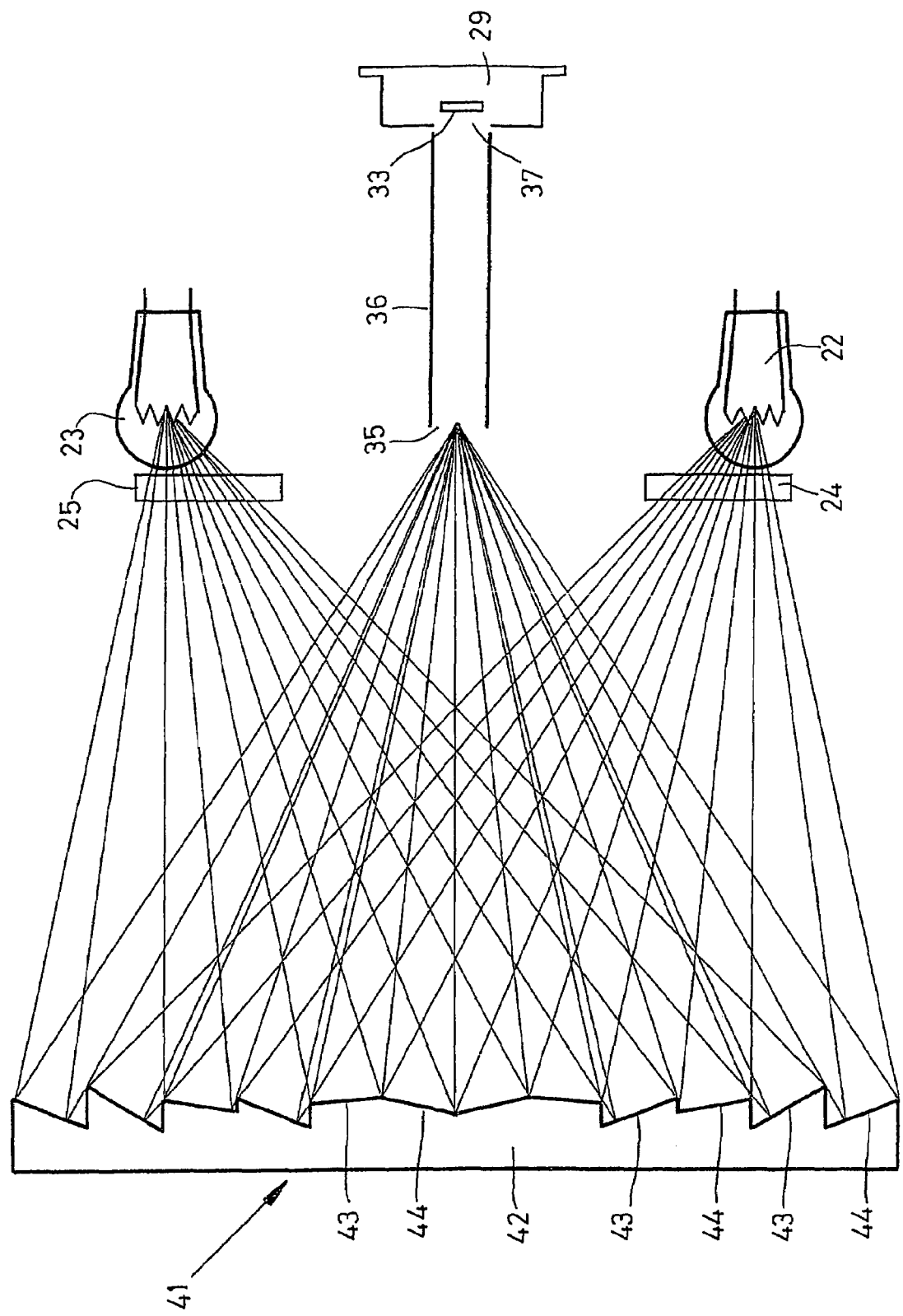
FIG. 4 is a schematic view of a third embodiment of a gas sensor according to the invention.

FIG. 4 shows a third embodiment of a gas sensor 41 according to the invention, which is different from the gas sensor 34 that is shown in FIG. 3 in that a faceted mirror 42 is provided instead of two mirrors 26, 27, the mirror surfaces 43 of which reflect the light from the light source 23 in the direction of the light entry opening 35, whilst the mirror surfaces 44 reflect light from the light source 23 in the direction of the light entry opening 35. Ageing and fouling of the faceted mirror 42 will occur to the same extent for both light sources 22, 23, so that the gas concentration as determined on the basis of the light source 23 can easily be corrected by means of the reference light source 23.

In addition, a symmetrical incidence of light on the light entry opening 35 is obtained by means of the faceted mirror, resulting in an optimised effect of the channel.

Figure 5:
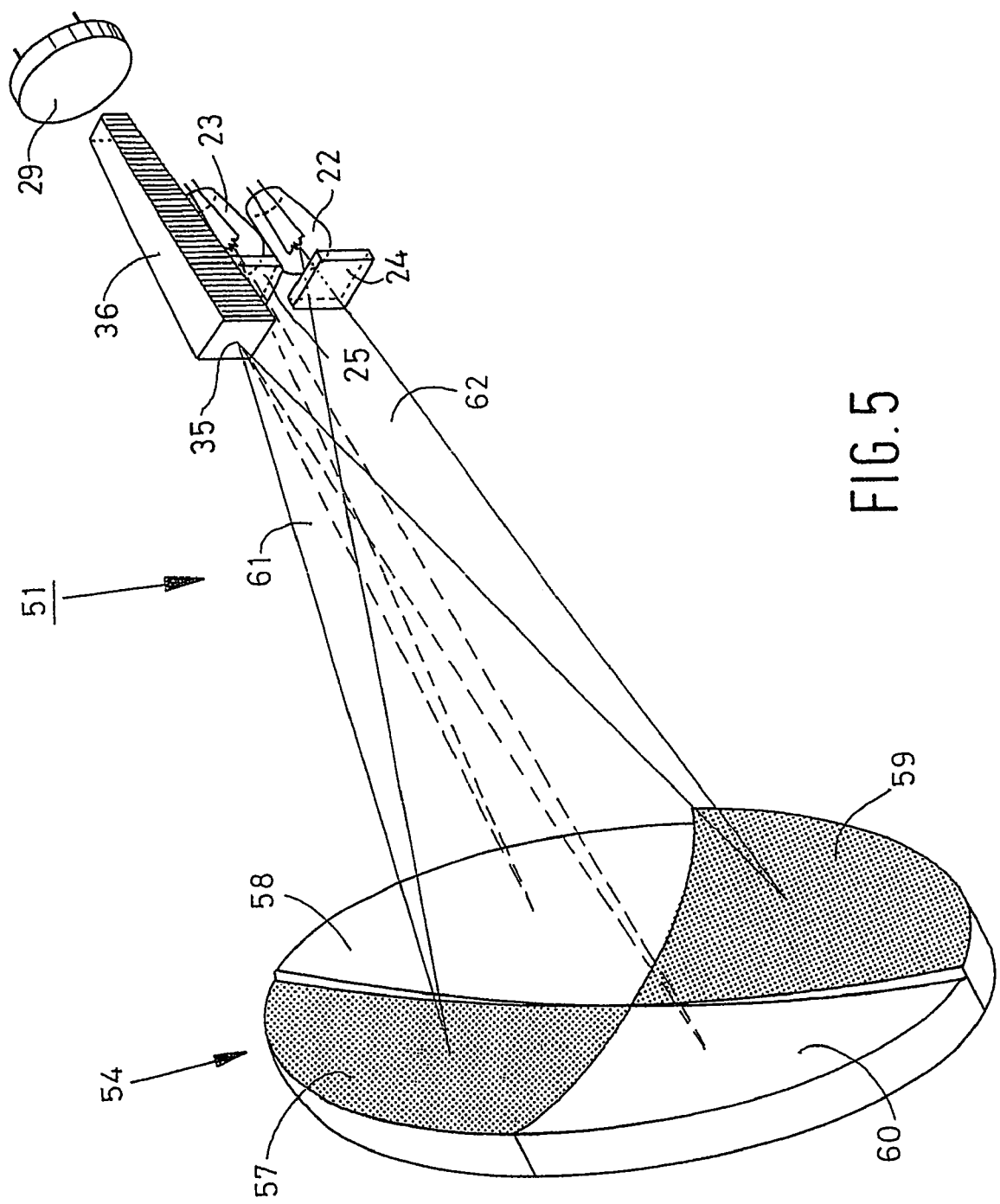
FIG. 5 is a schematic view of a fourth embodiment of a gas sensor according to the invention.

FIG. 5 shows a fourth embodiment of a gas sensor 51 according to the invention, which is provided with a detector 29, a light-reflecting, channel-shaped chamber 36, a segmented, faceted mirror 54 and two light sources 22, 23, in front of each of which light source 22, 23 a filter 24, 25 is disposed. The channel-shaped chamber 36 is of square cross-section, with the cross-sectional area of the chamber 6 decreasing in the direction from the mirror 54 to the detector 29. The light sources 22, 23 are disposed relatively close together on the same side of the chamber 36. The mirror 54 comprises four segments 57, 58, 59, 60, which are more or less symmetrically distributed over the area of the mirror 54. The segments 57, 59 form a first group of segments, which cooperate with the light source 22, whilst the segments 58, 60 form a second group of segments, which cooperate with the light source 23. The two groups of segments have two different focal points.

The light beams 61, 62 from the light sources 22, 23 are projected on the light entry opening 35 of the light-reflecting chamber 36 via the segments 58, 60 and 57, 59, respectively. Subsequently, the light is homogenised in the channel-shaped chamber 36 and analysed by means of the detector 29.

The distance between the light sources 22, 23 and the mirror 54 depends on the gas that is to be detected and the concentration thereof.

It is also possible to use three or more light sources, which makes it possible to detect different gases with a gas sensor.

It is also possible to provide the faceted mirror with fewer or with more mirror surfaces.

It is also possible, of course, to use other gases than $CO_2$ by means of the gas sensor according to the invention, with the filter 24 for example transmitting light having a wavelength of 4.64 μm for CO or 3.4 μm for HC.

It is also possible to project the light source on an enlarged scale, on the same scale or on a reduced scale on the light entry opening.

While the invention has been described and illustrated in its preferred embodiments, it should be understood that departures may be made therefrom within the scope of the invention, which is not limited to the details disclosed herein.

What is claimed is:

1. A gas sensor comprising at least two light sources, projection optics and a light-reflecting chamber provided with at least one light entry opening, which gas sensor further comprises a detector that cooperates with the chamber, by means of which detector light from the light source can be detected, wherein the at least two light sources can each be projected on a light entry opening of the chamber by means of said projection optics, and wherein the cross-sectional area of the chamber gradually decreases from the light entry opening in the direction of the detector.

2. The gas sensor of claim 1, wherein the projection optics project each of the light sources on a reduced scale on a light entry opening of the chamber.

3. The gas sensor of claim 1, wherein the at least two light sources can each be projected on the same light entry opening of the chamber by means of projection optics.

4. The gas sensor of claim 3, wherein the light paths between the light sources and the detector are substantially identical.

5. The gas sensor of claim 1, wherein the projection optics comprises at least one projection mirror.

6. The gas sensor of claim 5, wherein the projection mirror is faceted.

7. The gas sensor of claim 5, wherein the mirror comprises a number of segments, a first group of which segments is used for projecting the first light source on the light entry opening whilst the second group of segments is used for projecting the second light source on the light entry opening.

8. The gas sensor of claim 7, wherein the two groups of segments have two different focal points.

9. The gas sensor of claim 1, wherein the light sources are disposed on the same side of the chamber.

10. The gas sensor of claim 1, wherein the light sources are spaced apart by a centre distance in the order of the diameter of the light sources.

11. The gas sensor of claim 1, comprising at least three light sources.

12. The gas sensor of claim 1, wherein the chamber is of square cross-section, at least one side of which cross-section has a dimension in the order of the dimension of a light-receiving element of the detector or of the dimension of the projection of the light source.

13. The gas sensor of claim 1, wherein the length of the chamber is at least three times greater than the cross-sectional dimension of the chamber.

14. The gas sensor of claim 1, wherein the chamber is channel-shaped, at least one dimension of the chamber being in the order of a dimension of a light-receiving surface of the detector.

15. The gas sensor of claim 1, wherein the chamber is provided with a light exit opening, near which light exit opening the detector is mounted.

16. The gas sensor of claim 1, wherein a wavelength-determining element is disposed between at least one light source and the detector.

17. The gas sensor of claim 16, wherein the wavelength-determining element is a filter.

18. The gas sensor of claim 16, wherein the wavelength-determining element is disposed between the light source and the projection optics.

19. The gas sensor of claim 16, wherein the wavelength-determining element is disposed between the projection optics and the detector.

20. A gas sensor comprising at least two light sources, projection optics and a light-reflecting chamber provided with at least one light entry opening, which gas sensor further comprises a detector that cooperates with the chamber, by means of which detector light from the light source can be detected, wherein the at least two light sources can each be projected on a light entry opening of the chamber by means of said projection optics, and wherein the projection optics comprises at least one faceted projection mirror.

21. A gas sensor comprising at least two light sources, projection optics and a light-reflecting chamber provided with at least one light entry opening, which gas sensor further comprises a detector that cooperates with the chamber, by means of which detector light from the light source can be detected, wherein the at least two light sources can each be projected on a light entry opening of the chamber by means of said projection optics, wherein the projection optics comprises at least one projection mirror comprising a number of segments, a first group of which segments being used for projecting the first light source on the light entry opening whilst the second group of segments is used for projecting the second light source on the light entry opening.

* * * * *